United States Patent [19]

Kume et al.

[11] Patent Number: 4,609,669

[45] Date of Patent: Sep. 2, 1986

[54] CARBAMOYLIMIDAZOLE DERIVATIVES AND FUNGICIDAL USE THEREOF

[75] Inventors: Toyohiko Kume, Hino; Yoshio Kurahashi, Hachioji; Kunihiro Isono; Shinji Sakawa, both of Hino; Noboru Matsumoto, Hachioji, all of Japan

[73] Assignee: Nihon Tokushu Noyaku Seizo K.K., Tokyo, Japan

[21] Appl. No.: 774,206

[22] Filed: Sep. 9, 1985

[30] Foreign Application Priority Data

Sep. 11, 1984 [JP] Japan ................................ 59-188778
Feb. 25, 1985 [JP] Japan ................................ 60-34642

[51] Int. Cl.$^4$ ..................... A01N 43/50; C07D 233/54
[52] U.S. Cl. ...................................... 514/399; 548/341
[58] Field of Search ......................... 548/341; 514/399

[56] References Cited

U.S. PATENT DOCUMENTS 4,353,921 10/1982 Diamond et al. .................... 548/341

FOREIGN PATENT DOCUMENTS 1469772 4/1977 United Kingdom ................ 548/341

Primary Examiner—Henry R. Jiles
Assistant Examiner—Robert C. Whittenbaugh
Attorney, Agent, or Firm—Sprung Horn Kramer & Woods

[57] ABSTRACT

Novel carbamoylimidazole derivatives of the formula (I)

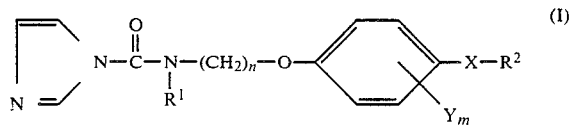

in which
$R^1$ represents lower alkyl, lower alkoxy-lower alkyl or cycloalkyl having 3 to 8 carbon atoms,
$R^2$ represents fluoro-substituted lower alkyl,
X represents oxygen or sulfur,
Y represents halogen or lower alkyl,
m represents the numbers 0, 1 or 2, and
n represents the numbers 2, 3, 4, 5 or 6, and the use of the new compounds as agricultural and horticultural fungicides.

8 Claims, No Drawings

CARBAMOYLIMIDAZOLE DERIVATIVES AND FUNGICIDAL USE THEREOF

The present invention relates to novel carbamoylimidazole derivatives, to processes for their preparations and to their use as agricultural and horticultural fungicides.

It has already been disclosed that certain carbamoylimidazole derivatives have fungicidal activities (see Japanese Laid-Open Patent Application No. 31047/1975, resp. Great Britain Patent Application No. 1 469 772).

There have been found novel carbamoylimidazole derivatives of the formula (I)

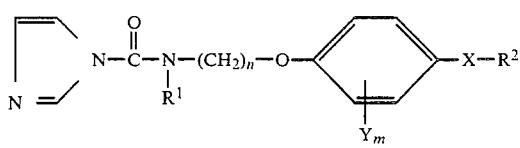

in which
- $R^1$ represents lower alkyl, lower alkoxy-lower alkyl or cycloalkyl having 3 to 8 carbon atoms,
- $R^2$ represents fluoro-substituted lower alkyl,
- X represents oxygen or sulfur,
- Y represents halogen or lower alkyl,
- m represents the numbers 0, 1 or 2, and
- n represents the numbers 2, 3, 4, 5 or 6.

Carbamoylimidazole derivatives of the formula (I) are obtained when (a) the compounds of the formula (II)

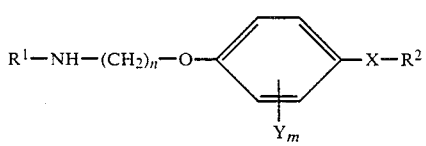

wherein $R^1$, $R^2$, X, Y, m and n are as defined above, are reacted with N,N'-carbonyldiimidazole of the formula

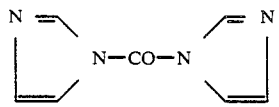

if appropriate in the presence of acid acceptors and inert solvents, or (b) the compounds of the formula (IV)

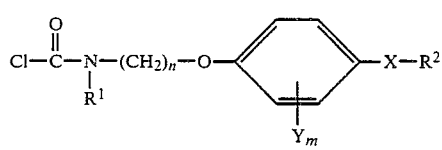

wherein $R^1$, $R^2$, X, Y, m and n are as defined above, are reacted with the imidazole compounds of the formula (V)

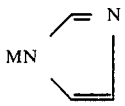

wherein M represents a hydrogen atom or an alkali metal atom, if appropriate in the presence of acid acceptors and inert solvents.

The novel carbamoylimidazole derivatives of the general formula (I) exhibit powerful agricultural and horticultural fungicidal properties.

Surprisingly, the compounds according to the invention exhibit a substantially greater fungicidal action in the field of agriculture and horticulture than those known from the aforementioned prior art.

Though the generic scope of the compounds of the aforementioned prior art conceptually embraced the compounds of the formula (I) according to the invention, the specification of the prior art fails to give any specific description or suggestion on the present invention.

Among the carbamoylimidazole derivatives of the formula (I), preferred compounds are those in which
- $R^1$ represents alkyl with 1 to 4 carbon atoms, alkoxyalkyl with altogether 2 to 4 carbon atoms or cycloalkyl with 5 to 6 carbon atoms,
- $R^2$ represents fluoroalkyl with 1 to 4 carbon atoms and 1 to 3 fluorine atoms,
- Y represents chlorine or methyl, and
- X, m and n have the meanings given above.

Particularly preferred are such compounds of the general formula (I), in which
- $R^1$ represents alkyl with 1 to 4 carbon atoms, alkoxyalkyl with altogether 2 to 4 carbon atoms or cyclopentyl,
- $R^2$ represents trifluoro-substituted alkyl with 1 to 4 carbon atoms,
- X represents oxygen or sulfur,
- Y represents chlorine or methyl,
- m represents the numbers 0, 1 or 2, and
- n represents the numbers 2, 3 or 4.

Very particularly preferred carbamoylimidazole derivatives of the formula (I) are those in which
- $R^1$ represents alkyl with 3 to 4 carbon atoms or ethoxyethyl,
- $R^2$ represents trifluoromethyl or 2,2,2-trifluoroethyl,
- X represents oxygen or sulfur,
- Y represents chlorine,
- m represents the numbers 0, 1 or 2 and
- n represents the number 2.

Specifically, the following compounds may be mentioned:

1-<N-2-[2,6-dichloro-4-(2,2,2-trifluoroethylthio)-phenoxy]-ethyl-N-propyl-carbamoyl>-imidazole, 1-<N-2-[2,6-dichloro-4-(2,2,2-trifluoroethylthio)-phenoxy]-ethyl-N-sec-butyl-carbamoyl>-imidazole, 1-[N-2-(4-trifluoromethylthiophenoxy)-ethyl-N-sec-butyl-carbamoyl]-imidazole, 1-<N-2-[2,6-dichloro-4-(trifluoromethylthio)-phenoxy]-ethyl-N-propyl-carbamoyl>-imidazole, 1-[N-3-(4-trifluoromethylthiophenoxy)-propyl-N-sec-butyl-carbamoyl]-imidazole, 1-[N-5-(4-trifluoromethylthiophenoxy)-pentyl-N-propyl-carbamoyl]-imidazole, 1-[N-2-(4-trifluoromethoxyphenoxy)-ethyl-N-propyl-carbamoyl]-imidazole, 1-[N-2-(2,6-dichloro-4-trifluoromethoxyphenoxy)-ethyl-N-propyl-carbamoyl]-imidazole and
1-[N-3-(4-trifluoromethoxyphenoxy)-propyl-N-sec.-butyl-carbamoyl]-imidazole.

If, for example, N-<2-[2,6-dichloro-4-(2,2,2-trifluoroethylthio)-phenoxy]-ethyl>-N-propylamine and N,N'-carbonyldiimidazole are used as starting materials, the course of the reaction variant (a) can be represented by the following equation:

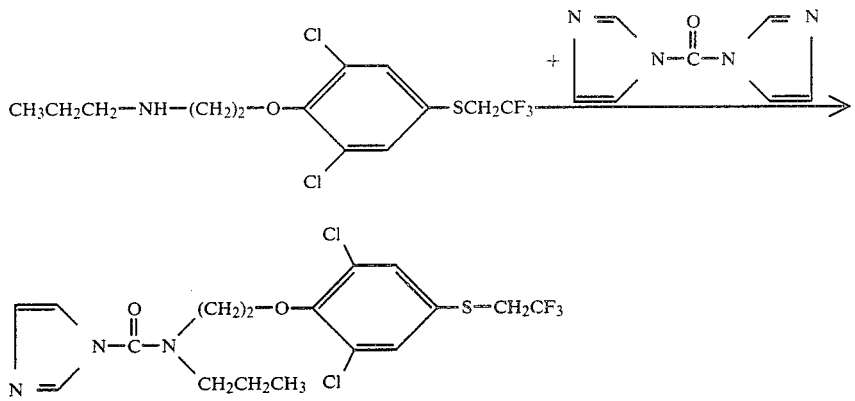

If, for example, N-(sec.-butyl)-N-[(4-trifluoromethoxy)-phenoxy-ethyl]-amidoformic acid chloride and imidazole are used as starting materials, the course of the reaction variant (b) can be represented by the following equation:

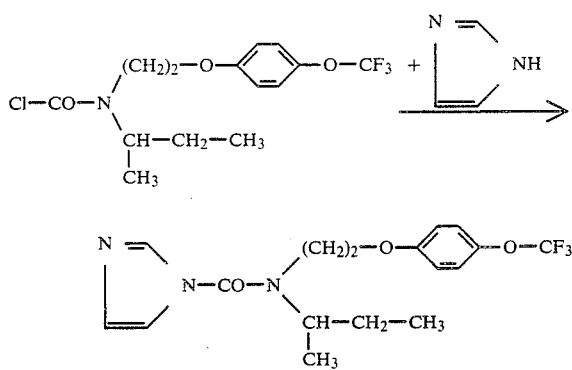

As starting materials in the reaction variant (a) according to the invention, the compounds of the general formula (II) are required. In this formula $R^1$, $R^2$, X, Y, m and n preferably have the meanings already given above in connection with the preferred meanings of the substituents in the general formula (I).

The compounds of the general formula (II) are novel and are obtained by reacting compounds of the formula (VI)

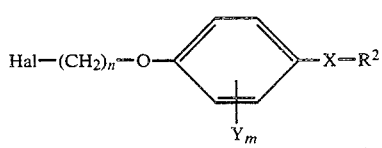

wherein
$R^2$, X, Y, m and n are as defined above, and
Hal represents a halogen atom, with amino compounds of the formula (VII)

$$R^1-NH_2 \qquad (VII)$$

wherein $R^1$ is as defined above.

The intermediates of the general formula (VI) are also novel. They are obtained when compounds of the formula (VIII)

wherein $R^2$, X, Y and m are as defined above, are reacted with dihalogeno compounds of the formula (IX)

$$Hal-(CH_2)_n-Hal \qquad (IX)$$

wherein n and Hal are as defined above, if appropriate, in presence of acid acceptors and inert solvents.

As examples of the novel intermediates of the formula (VI) the following compounds may be mentioned:
2-[4-(2,2,2-trifluoroethylthio)-phenoxy]-ethyl bromide,
2-[4-(2,2,2-trifluoroethylthio)-2-tolyloxy]-ethyl bromide,
2-[4-(2,2,2-trifluoroethylthio)-3,5-xylyloxy]-ethyl bromide,
2-[2-chloro-4-(2,2,2-trifluoroethylthio)-phenoxy]ethyl bromide,
2-[2,6-dichloro-4-(2,2,2-trifluoroethylthio)-phenoxy]-ethyl bromide
3-[4-(2,2,2-trifluoroethylthio)-phenoxy]-propyl bromide
3-[2,6-dichloro-4-(2,2,2-trifluoroethylthio)-phenoxy]-propyl bromide,
4-[4-(2,2,2-trifluoroethylthio)-phenoxy]-butyl bromide,
4-[4-(2,2,2-trifluoroethylthio)-2-tolyloxy]-butyl bromide,
4-[4-(2,2,2-trifluoroethylthio)-3,5-xylyloxy]-butyl bromide,
4-[2-chloro-4-(2,2,2-trifluoroethylthio)-phenoxy]butyl bromide,
2-(4-trifluoromethylthiophenoxy)-ethyl bromide,
2-(2-chloro-4-trifluoromethylthiophenoxy)-ethyl bromide,
2-(2,6-dichloro-4-trifluoromethylthiophenoxy)-ethyl bromide,
3-(4-trifluoromethylthiophenoxy)-propyl bromide, 3-(2-chloro-4-trifluoromethylthiophenoxy)-propyl bromide,
3-(2,6-dichloro-4-trifluoromethylthiophenoxy)-propyl bromide,
4-(4-trifluoromethylthiophenoxy)-butyl bromide,
4-(2-chloro-4-trifluoromethylthiophenoxy)-butyl bromide,
2-(4-trifluoromethoxyphenoxy)-ethyl bromide
2-(2-chloro-4-trifluoromethoxyphenoxy)-ethyl bromide,
2-(2,6-dichloro-4-trifluoromethoxyphenoxy)-ethyl bromide,
3-(4-trifluoromethoxyphenoxy)-propyl bromide,
3-(2-chloro-4-trifluoromethoxyphenoxy)-propyl bromide, and
3-(2,6-dichloro-4-trifluoromethoxyphenoxy)-propyl bromide.

The compounds of the formula (VIII) are partically already known (see Japanese Laid-Open Patent Application Nos. 222094/1983 and 151151/1977. As example, there may be mentioned:
4-(2,2,2-trifluoroethylthio)-phenol,
4-(2,2,2-trifluoroethylthio)-2-methyl-phenol
4-(2,2,2-trifluoroethylthio)-3,5-dimethyl-phenol,
2-chloro-4-(2,2,2-trifluoroethylthio)-phenol,
2,6-dichloro-4-(2,2,2-trifluoroethylthio)-phenol,
4-trifluoromethylthio-phenol,
2-chloro-4-trifluoromethylthio-phenol,
2,6-dichloro-4-trifluoromethylthio-phenol,
4-trifluoromethoxy-phenol,
2-chloro-4-trifluoromethoxy-phenol and
2,6-dichloro-4-trifluoromethoxy-phenol.

Some of these compounds are novel. As an example, 2,6-dichloro-4-(2,2,2-trifluoroethylthio)-phenol is novel and may be prepared by using the well-known 2,6-dichlorophenol (see Beilstein, main volume (Hauptwerk) H6, page 190) as starting material, which is reacted with chlorosulfonic acid and the 2,6-dichloro-4-chlorosulfonyl-phenol obtained is reduced with zinc and sulfuric acid, and the 2,6-dichloro-4-mercapto-phenol obtained is reacted thereafter with 2,2,2-trifluoroethyl benzenesulfonate in the presence of potassium carbonate in dimethylformamide, resulting in the novel compound of the formula

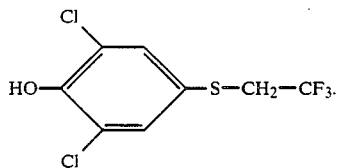

The processes mentioned above are already known in general (see, for example, J. Org. Chem. 31, 2672–74 (1966) and Organic Syntheses, Coil. Vol. 1, pages 504–506).

2,6-Dichloro-4-trifluoromethylthio-phenol is also novel and may be produced by using trifluoroiodomethane in place of 2,2,2-trifluoroethyl-benzenesulfonate in accordance with the above-mentioned reaction.

2,6-Dichloro-4-trifluoromethoxy-phenol is also novel and the course of the reactions for its preparation can be explained as follows: 4-(Trifluoromethoxy)-phenol which is already known (see J. Org. Chem. 44, 2907–10 (1979)) is chlorinated in carbon tetrachloride yielding 2-chloro-4-(trifluoromethoxy)-phenol (at about 20° to 30° C.) and 2,6-dichloro-4-(trifluoromethoxy)-phenol (at the boiling point of the reaction mixture).

The dihalogeno-compounds of the general formula (IX) are well-known, as examples there may be mentioned:
Ethylene bromide,
propylene bromide, and
butylene bromide.

The formula (VII) provides a general definition of the amino compounds required as primary products in the reaction variant (a). In this formula $R^1$ preferably has the meanings already given above. As examples of the well known compounds of the formula (VII) may be mentioned:
methylamine,
ethylamine,
n-propylamine,
iso-propylamine,
n-butylamine,
sec.-butylamine,
2-ethoxyethylamine,
cyclopentylamine, and
cyclohexylamine.

The compounds of the general formula (II) explained above in connection with the reaction variant (a) are also starting materials needed to prepare the compounds of the general formula (IV). The last-mentioned compounds which are the starting materials in the reaction variant (b) are obtained by reaction of the novel compounds of the general formula (II) with phosgene or with diphosgene (i.e. trichloromethyl chloroformate), preferably in a solvent such as benzene or toluene at temperatures between 40° and 120° C. (see also the preparation examples).

The imidazolyl compounds of the formula (V) are also needed as starting materials in the reaction variant (b) according to the instant invention.

In this formula M preferably means hydrogen (this means imidazole itself is preferred), sodium and potassium.

The process for the production of the compounds of the general formula (I) according to process varant (a) may be carried out desirably in a solvent or diluent. Suitable diluents are all inert solvents. These include water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and ethyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The process according to variant (a) may be carried out in the presence of an acid acceptor. Examples of acid acceptors include the hydroxides, carbonates, bicarbonates and alcoholates of alkali metals and tertiary amines such as triethylamine, diethylaniline and pyridine, all of which are generally known.

The process according to variant (a) can be carried out over a wide temperature range. Generally, it can be carried out at a temperature between about −20° C. and the boiling point of the mixture, desirably between about 0° C. and about 100° C. Desirably, the reaction is carried out under normal atmospheric pressure, but it is also possible to operate under elevated or reduced pressures.

In carrying out reaction variant (a) according to the invention, said reaction may be carried out without separating the compounds of the formula (II) as an intermediate. Alternatively, said intermediates of the formula (II) may also be separated.

Reaction variant (b) according to the invention is preferably carried out in the presence of a solvent or diluent. Preferred solvents or diluents in the process are any of inert solvents as described hereinbefore for reaction variant (a). Likewise, reaction variant (b) is preferably carried out in the presence of acid acceptors as described above for reaction variant (a).

Reaction variant (b) can be carried out over a wide temperature range, for example at a temperature between −20° C. and the boiling point of the mixture, preferably between 0° and 100° C. The reaction variant (b) is carried out under normal (ambient) pressure, but it is also possible to operate under elevated or reduced pressures.

The reaction for the preparation of the novel intermediates of the general formula (VI), i.e. the reaction of the compounds of the formula (VIII) with the dihalogeno compounds of the formula (IX), are also preferably carried out in the presence of a solvent or diluent. Preferred solvents or diluents in the process are any of inert solvents as described hereinbefore for reaction variant (a). Likewise, the reaction is preferably carried out in the presence of an acid acceptor as described hereinbefore for reaction variant (a). The temperatures can be held within a wide range, for example at a temperature between −20° C. and the boiling point of the mixture, preferably between 0° and 100° C. The reaction is carried out under normal (ambient) pressure, but it is also possible to operate under elevated or reduced pressures.

The carbamoylimidazole derivatives according to the invention exhibit powerful fungicidal effects in the field of agriculture and horticulture. They can therefore be used as agricultural and horticultural fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bacterial agents are employed in plant protection for combating Pseudomonadaceae, Rhizobiaceae, Enterobacteriaceae, Corynebacteriaceae and Streptomycetaceae.

Some causative organisms of fungal and bacterial diseases which fall under generic names listed above may be mentioned as examples, but not by way of limitation: Botrytis species, such as, for example, *Botrytis cinerea;* Plasmopara species, such as, for example, *Plasmopara viticola;* Uromyces species, such as, for example, *Uromyces appendiculatus;* Sphaerotheca species, such as, for example, *Sphaerotheca fuliginea;* Venturia species, such as, for example, *Venturia inaequalis;* Podosphaera species, such as, for example, *Podosphaera leucotricha;* Phytophthora species, such as, for example, *Phytophthora infestans;* Erysiphe species, such as, for example, *Erysiphe graminis;* Puccinia species, such as, for example, *Puccinia recondita;* Fusarium species, such as, for example, *Fusarium culmorum;* Ustilago species, such as, for example, *Ustilago nuda* or *Ustilago avenae;* Septoria species, such as, for example, *Septoria nodorum;* Tilletia species, such as, for example, *Tilletia caries;* Xanthomonas species, such as, for example, *Xanthomonas oryzae;* Pseudomonas species, such as, for example, *Pseudomonas lachrymans;* Pyricularia species, such as, for example, *Pyricularia oryzae,* Pellicularia species, such as, for example, *Pellicularia sasakii;* Pyrenophora species, such as, for example, *Pyrenophora teres* (conidia form Drechslera, Syn. Helminthosporium); Cochliobolus species, such as, for example, *Cochliobolus sativus* (conidia form Drechslera, Syn. Helminthosporium); Cercospora species, such as, for example, *Cercospora canescens.*

In particular, the carbamoylimidazole derivatives according to the general formula (I) exhibit an outstanding efficacy against blast of rice (*Pyricularia oryzae*), brown spot of rice (*Helminthosporium oryzae*), "bakanae" disease of rice (*Gibberella fujikuroi*), stem rot (*Sclerotinia sclerotiorum*), leaf blight (*Alternaria brassicae*), powdery mildew (*Sphaerotheca fuliginea*) and gray mold (*Botrytis cinerea*) of various crops, anthracnose (*Colletotrichum lagenarium*) of cucumber, melon and the like, and late blight (*Phytophthora infestans*) of tomato.

As an agricultural and horticultural fungicide, the compounds of the formula (I) in accordance with this invention may be used directly upon dilution with water, or in various formulations obtained by methods generally practiced in the production of agricultural chemicals using agriculturally acceptable adjuvants. In actual use, these various formulations may be applied directly or after diluting them with water to the desired concentrations.

The agricultural acceptable adjuvants as referred to herein include, for example, diluents (solvents, extenders, carriers), surface-active agents (solubilizing agents, emulsifiers, dispersing agents, wetting agents), stabilizers, stickers, aerosol propellants and synergists.

Examples of the solvents are water; furthermore organic solvents, such as hydrocarbons, for example n-hexane, petroleum ether, petroleum fractions, for example paraffin waxes, kerosene, light oils, middle oils and heavy oils, benzene, toluene, and xylene, furthermore halogenated hydrocarbons such as methylene chloride, carbon tetrachloride, ethylene chloride, ethylene dibromide, chlorobenzene and chloroform, alcohols such as methanol, ethanol, propanol and ethylene glycol, ethers such as diethyl ether, ethylene oxide and dioxane, alcohol ethers such as ethylene glycol monomethyl ether, ketones such as acetone and isophorone, esters such as ethyl acetate and amyl acetate, amides such as dimethylformamide and dimethylacetamide and sulfoxides such as dimethyl sulfoxide.

Examples of the extenders or carriers include inorganic powders, for example sulfur, slaked lime, magnesium lime, gypsum, calcium carbonate, silica, perlite, pumice, calcite, diatomaceous earth, amorphous silica, alumina, zeolites, and clay minerals (such as pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfonic acid esters (such as sodium laurylsulfate), arylsulfonic acids (such as alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (for example laurylamine, stearyl trimethyl ammonium chloride and alkyl dimethylbenzyl ammonium chloride) and polyoxyethylene alkylamines; nonionic surface-active agents such as polyoxyethylene glycol ethers (for example polyoxyethylene alkylaryl ethers and the condensation products thereof), polyoxyethylene glycol esters (for example polyoxyethylene fatty acid esters), and polyhydric alcohol esters for example polyoxyethylene sorbitan monolaurate); and amphoteric surface-active agents.

Examples of other adjuvants include stabilizers; stickers (such as agricultural soaps, casein lime, sodium alginate, polyvinyl alcohol, vinyl acetate-type adhesives and acrylic adhesives); aerosol propellants (such as trichlorofuoromethane, dichlorofluoromethane, 1,2,2-trichloro-1,1,2-trifluoroethane, chlorobenzene, and lower ethers); combustion controlling agents for fumigants (such as nitrites, zinc powder, and dicyandiamide); oxygen-yielding agents (such as chlorates); effect-prolonging agents; dispersion stabilizers (such as casein, tragacanth, carboxymethyl cellulose and polyvinyl alcohol); and synergists.

The compounds of this invention can be formulated into various forms by methods generally practiced in the production of agricultural chemicals. Illustrative of such forms are emulsifiable concentrates, oil preparations, wettable powders, soluble powders, suspensions, dusts, granules, pulverulent preparations, fumigants, tablets, aerosols, pastes and capsules.

The agricultural and horticultural fungicide of this invention may contain about 0.1 to about 95% by weight, preferably about 0.5 to about 90% by weight, of the aforesaid active ingredient.

In actual use, the suitable amount of the active compound in the aforesaid various formulations and ready-to-use preparations is generally about 0.0001 to about 20% by weight, preferably about 0.005 to about 10% by weight.

The content of the active ingredient can be properly varied depending upon the type of the formulation, the method, purpose, time and locus of its application, the state of occurrence of diseases.

If required, the compounds of this invention may be used in combination with other agricultural chemicals, for example insecticides, other fungicides, miticides, nematocides, antiviral agents, herbicides, plant growth regulators and attractants, such as organophosphate compounds, carbamate compounds, dithio (or thiol) carbamate compounds, organochlorine compounds, dinitro compounds, organosulfur or organometallic compounds, antibiotics, substituted diphenyl ether compounds, urea compounds, and triazine compounds, and/or fertilizers.

Various formulations and ready-to-use preparations containing the aforesaid active ingredient of the invention can be applied by various methods generally practiced in the field of agricultural chemical application, for example spraying (liquid spraying, misting, atomizing, dusting, granule scattering, water surface application, pouring, etc.); soil application (mixing, sprinkling, vaporing and pouring etc.); surface application (such as coating, banding, dust coating and covering); and dipping. It can also be used by the so-called ultralow volume spraying method. According to this method, the active ingredient may be used in an amount of almost 100%.

The reate of application per unit area can be properly chosen, and is, for example, about 0.03 to about 10 kg, preferably about 0.3 to about 6 kg, per hectare.

According to this invention, there can be provided an agricultural and horticultural fungicidal composition comprising the compound of general formula (I) as an active ingredient and a diluent (a solvent and/or an extender and/or a carrier) and/or a surface-active agent, and if further required, a stabilizer, a sticker and a synergist.

This invention also provides a method for controlling a crop disease, which comprises applying to a pathogen and/or the locus of its occurrence and/or the locus of occurrence of a crop disease, the compound of general formula (I) either singly or in admixture with a diluent (a solvent and/or an extender and/or a carrier) and/or surface-active agent and if further required, a stabilizer, a sticker and a synergist.

The following examples illustrate the present invention specifically. It should be noted however that the invention is not limited to them alone.

PREPARATION EXAMPLES

Example 1

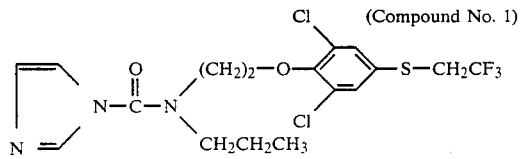
(Compound No. 1)

To 2.16 g of crude N-<2-[2,6-dichloro-4-(2,2,2-trifluoroethylthio)-phenoxy]-ethyl>-N-(propyl)-amine were added 10 ml of toluene and 1.7 g of N,N'-carbonyldiimidazole. The mixture was stirred at 50° C. for 3 hours and then under reflux for 6 hours. After cooling, 60 ml of toluene were added. The mixture was washed with water and dried over anhydrous sodium sulfate. Evaporation of toluene gave 2.2 g of 1-<N-2-[2,6-dichloro-4-(2,2,2-trifluoroethylthio)-phenoxy]-ethyl-N-propyl-carbamoyl>-imidazole with the refractive index of $n_D^{20} = 1.5491$.

The following compounds of the general formula (I)

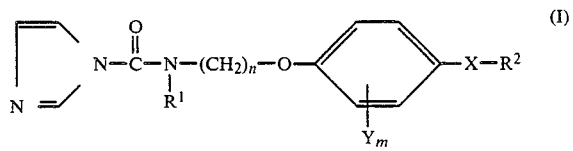
(I)

were obtained by the method described in Example 1:

| Compound No. | $R^1$ | n | $Y_m$ | $X-R^2$ | Physical constant |
|---|---|---|---|---|---|
| 2 | —CH$_3$ | 2 | — | —SCH$_2$CF$_3$ | $n_D^2 = 1.5462$ |
| 3 | —C$_2$H$_5$ | 2 | — | —SCH$_2$CF$_3$ | $n_D^2 = 1.5395$ |
| 4 | —C$_3$H$_7$—iso | 2 | — | —SCH$_2$CF$_3$ | $n_D^2 = 1.5314$ |

-continued

| Compound No. | $R^1$ | n | $Y_m$ | $X-R^2$ | Physical constant |
|---|---|---|---|---|---|
| 5 | $-C_3H_7-n$ | 2 | — | $-SCH_2CF_3$ | $n_D^2 = 1.5332$ |
| 6 | $-C_4H_9-sec$ | 2 | — | $-SCH_2CF_3$ | $n_D^2 = 1.5295$ |
| 7 | $-C_4H_9-n$ | 2 | — | $-SCH_2CF_3$ | $n_D^2 = 1.5256$ |
| 8 | $-C_2H_4OC_2H_5$ | 2 | — | $-SCH_2CF_3$ | $n_D^2 = 1.5274$ |
| 9 | cyclopentyl-H | 2 | — | $-SCH_2CF_3$ | $n_D^2 = 1.5460$ |
| 10 | $-C_3H_7-n$ | 2 | 2-$CH_3$ | $-SCH_2CF_3$ | $n_D^2 = 1.5345$ |
| 11 | $-C_4H_9-sec$ | 2 | 2-$CH_3$ | $-SCH_2CF_3$ | $n_D^2 = 1.5313$ |
| 12 | $-C_4H_9-sec$ | 2 | 3,5-$(CH_3)_2$ | $-SCH_2CF_3$ | $n_D^2 = 1.5330$ |
| 13 | $-C_3H_7-n$ | 2 | 2-Cl | $-SCH_2CF_3$ | $n_D^2 = 1.5462$ |
| 14 | $-C_4H_9-sec$ | 2 | 2-Cl | $-SCH_2CF_3$ | $n_D^2 = 1.5420$ |
| 15 | $-C_4H_9-sec$ | 2 | 2,6-$Cl_2$ | $-SCH_2CF_3$ | $n_D^2 = 15460$ |
| 16 | cyclopentyl-H | 2 | 2,6-$Cl_2$ | $-SCH_2CF_3$ | $n_D^2 = 1.5592$ |
| 17 | $-C_3H_7-n$ | 3 | — | $-SCH_2CF_3$ | $n_D^2 = 1.5310$ |
| 18 | $-C_4H_9-sec$ | 3 | — | $-SCH_2CF_3$ | $n_D^2 = 1.5260$ |
| 19 | cyclopentyl-H | 3 | — | $-SCH_2CF_3$ | $n_D^2 = 1.5415$ |
| 20 | $-C_3H_7-n$ | 3 | 2,6-$Cl_2$ | $-SCH_2CF_3$ | $n_D^2 = 1.5498$ |
| 21 | $-C_4H_9-sec$ | 3 | 2,6-$Cl_2$ | $-SCH_2CF_3$ | $n_D^2 = 1.5430$ |
| 22 | cyclopentyl-H | 3 | 2,6-$Cl_2$ | $-SCH_2CF_3$ | $n_D^2 = 1.5570$ |
| 23 | $-C_3H_7-n$ | 4 | — | $-SCH_2CF_3$ | $n_D^2 = 1.5260$ |
| 24 | $-C_4H_9-sec$ | 4 | — | $-SCH_2CF_3$ | $n_D^2 = 1.5252$ |
| 25 | cyclopentyl-H | 4 | — | $-SCH_2CF_3$ | $n_D^2 = 1.5390$ |
| 26 | $-C_3H_7-n$ | 4 | — | $-SCH_2CF_3$ | $n_D^2 = 1.5280$ |
| 27 | $-C_4H_9-sec$ | 4 | 2-$CH_3$ | $-SCH_2CF_3$ | $n_D^2 = 1.5250$ |
| 28 | $-C_3H_7-n$ | 4 | 3,5-$(CH_3)_2$ | $-SCH_2CF_3$ | $n_D^2 = 1.5300$ |
| 29 | $-C_4H_9-sec$ | 4 | 3,5-$(CH_3)_2$ | $-SCH_2CF_3$ | $n_D^2 = 1.5266$ |
| 30 | $-C_3H_7-n$ | 4 | 2-Cl | $-SCH_2CF_3$ | $n_D^2 = 1.5380$ |
| 31 | $-C_4H_9-sec$ | 4 | 2-Cl | $-SCH_2CF_3$ | $n_D^2 = 1.5358$ |
| 32 | $-C_3H_7-n$ | 5 | — | $-SCH_2CF_3$ | $n_D^2 = 1.5260$ |
| 33 | $-C_4H_9-sec$ | 5 | — | $-SCH_2CF_3$ | $n_D^2 = 1.5245$ |
| 34 | $-C_4H_9-sec$ | 5 | 2,6-$Cl_2$ | $-SCH_2CF_3$ | $n_D^2 = 1.5395$ |
| 35 | $-C_3H_7-n$ | 6 | — | $-SCH_2CF_3$ | $n_D^2 = 1.5245$ |
| 36 | $-C_3H_7-n$ | 2 | — | $-SCF_3$ | m.p. 81-82° C. |
| 37 | $-C_4H_9-sec$ | 2 | — | $-SCF_3$ | $n_D^2 = 1.5247$ |
| 38 | cyclopentyl-H | 2 | — | $-SCF_3$ | m.p. 90-91° C. |
| 39 | cyclohexyl-H | 2 | — | $-SCF_3$ | $n_D^2 = 1.5375$ |
| 40 | $-C_3H_7-n$ | 2 | 2-Cl | $-SCF_3$ | m.p. 98-99° C. |
| 41 | $-C_4H_9-sec$ | 2 | 2-Cl | $-SCF_3$ | $n_D^2 = 1.5240$ |
| 42 | $-C_3H_7-n$ | 2 | 2,6-$Cl_2$ | $-SCF_3$ | $n_D^2 = 1.5410$ |
| 43 | $-C_4H_9-sec$ | 2 | 2,6-$Cl_2$ | $-SCF_3$ | $n_D^2 = 1.5188$ |
| 44 | cyclopentyl-H | 2 | 2,6-$Cl_2$ | $-SCF_3$ | $n_D^2 = 1.5483$ |
| 45 | $-C_3H_7-n$ | 3 | — | $-SCF_3$ | $n_D^2 = 1.5220$ |
| 46 | $-C_4H_9-sec$ | 3 | — | $-SCF_3$ | $n_D^2 = 1.5142$ |
| 47 | cyclopentyl-H | 3 | — | $-SCF_3$ | m.p. 83-84° C. |
| 48 | $-C_3H_7-n$ | 3 | 2-Cl | $-SCF_3$ | m.p. 101-102° C. |
| 49 | $-C_4H_9-sec$ | 3 | 2-Cl | $-SCF_3$ | $n_D^2 = 1.5284$ |
| 50 | $-C_3H_7-n$ | 3 | 2,6-$Cl_2$ | $-SCF_3$ | $n_D^2 = 1.5390$ |
| 51 | $-C_4H_9-sec$ | 3 | 2,6-$Cl_2$ | $-SCF_3$ | $n_D^2 = 1.5341$ |
| 52 | cyclopentyl-H | 3 | 2,-$Cl_2$ | $-SCF_3$ | m.p. 92-93° C. |
| 53 | $-C_3H_7-n$ | 4 | — | $-SCF_3$ | $n_D^2 = 1.5225$ |
| 54 | $-C_4H_9-sec$ | 4 | — | $-SCF_3$ | $n_D^2 = 1.5170$ |

-continued

| Compound No. | R¹ | n | Y_m | X—R² | Physical constant |
|---|---|---|---|---|---|
| 55 | cyclopentyl-H | 4 | — | —SCF₃ | $n_D^2 = 1.5330$ |
| 56 | —C₃H₇—n | 4 | 2-Cl | —SCF₃ | $n_D^2 = 1.5310$ |
| 57 | —C₄H₉—sec | 4 | 2-Cl | —SCF₃ | $n_D^2 = 1.5298$ |
| 58 | —C₃H₇—n | 5 | — | —SCF₃ | $n_D^2 = 1.5209$ |
| 59 | —C₄H₉—sec | 5 | — | —SCF₃ | $n_D^2 = 1.5186$ |
| 60 | cyclopentyl-H | 5 | — | —SCF₃ | $n_D^2 = 1.5303$ |
| 61 | —C₃H₇—n | 5 | 2-Cl | —SCF₃ | $n_D^2 = 1.5291$ |
| 62 | —C₄H₉—sec | 5 | 2-Cl | —SCF₃ | $n_D^2 = 1.5273$ |
| 63 | —C₄H₉—sec | 5 | 2,6-Cl₂ | —SCF₃ | $n_D^2 = 1.5323$ |
| 64 | —C₃H₇—n | 2 | — | —OCF₃ | $n_D^2 = 1.5000$ |
| 65 | —C₄H₉—sec | 2 | — | —OCF₃ | $n_D^2 = 1.4963$ |
| 66 | —C₃H₇—n | 2 | 2-Cl | —OCF₃ | m.p. 77–78° C. |
| 67 | —C₄H₉—sec | 2 | 2-Cl | —OCF₃ | $n_D^2 = 1.5044$ |
| 68 | —C₃H₇—n | 2 | 2,6-Cl₂ | —OCF₃ | $n_D^2 = 1.5163$ |
| 69 | —C₄H₉—sec | 2 | 2,6-Cl₂ | —OCF₃ | $n_D^2 = 1.5122$ |
| 70 | cyclopentyl-H | 2 | 2,6-Cl₂ | —OCF₃ | $n_D^2 = 1.5275$ |
| 71 | —C₃H₇—n | 3 | — | —OCF₃ | $n_D^2 = 1.4978$ |
| 72 | —C₄H₉—sec | 3 | — | —OCF₃ | $n_D^2 = 1.4947$ |
| 73 | —C₃H₇—n | 3 | 2-Cl | —OCF₃ | $n_D^2 = 1.5097$ |
| 74 | —C₄H₉—sec | 3 | 2-Cl | —OCF₃ | $n_D^2 = 1.5057$ |
| 75 | —C₃H₇—n | 3 | 2,6-Cl₂ | —OCF₃ | $n_D^2 = 1.5146$ |
| 76 | —C₄H₉—sec | 3 | 2,6-Cl₂ | —OCF₃ | $n_D^2 = 1.5112$ |
| 77 | cyclopentyl-H | 3 | 2,6-Cl₂ | —OCF₃ | m.p 80–82° C. |
| 78 | —C₃H₇—n | 5 | — | —OCF₃ | $n_D^2 = 1.4955$ |
| 79 | —C₄H₉—sec | 5 | — | —OCF₃ | $n_D^2 = 1.4942$ |
| 80 | —C₃H₇—n | 5 | 2-Cl | —OCF₃ | $n_D^2 = 1.5050$ |
| 81 | —C₄H₉—sec | 5 | 2-Cl | —OCF₃ | $n_D^2 = 1.5036$ |
| 82 | —C₃H₇—n | 5 | 2,6-Cl₂ | —OCF₃ | $n_D^2 = 1.5096$ |
| 83 | —C₄H₉—sec | 5 | 2,6-Cl₂ | —OCF₃ | $n_D^2 = 1.5075$ |
| 84 | cyclopentyl-H | 5 | 2,6-Cl₂ | —OCF₃ | $n_D^2 = 1.5160$ |

Note:
The symbol "—" in the column of Y_m means there is no Y-substituent and the meaning of m is 0 (zero).

PREPARATION OF THE STARTING PRODUCTS (preparation of compounds of the general formulae II, VI and VIII)

Example II-1

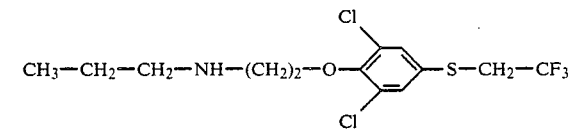

5 g of n-Propylamine were added to 2.38 g of 2-[2,6-dichoro-4-(2,2,2-trifluoroethylthio)-phenoxy]-ethyl bromide, and the mixture was stirred at room temperature for 8 hours and then under reflux for 3 hours. The excess of n-propylamine was evaporated. To the residue were added 20 ml of water, 20 ml of a 5% aqueous solution of potassium hydroxide and 100 ml of toluene. The mixture was stirred, and the organic layer was separated, washed with water and dried over anhydrous sodium sulfate. Low-boiling compounds were evaporated under reduced pressure. There were obtained 2.16 g of crude N-{2-[2,6-dichloro-4-(2,2,2-trifluoroethylthio)-phenoxy]-ethyl}-N-(propyl)amine having a refractive indes of $n_D^2 O = 1.5210$, which were used without further purification) for the preparation of compound No. 1 shown above.

Example VI-1

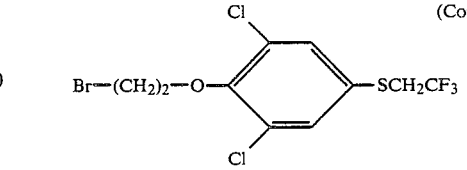
(Compound VI-1)

To an ethanol solution of sodium ethylate obtained by dissolving 0.7 g of metallic sodium in 50 ml of ethanol were added 8.9 g of 2,6-dichloro-4-(2,2,2-trifluoroethylthio)-phenol and 20 g of ethylene bromide. The mixture was stirred at 40° C. for 2 hours and under reflux for 4 hours. Ethanol and the excess of ethylene bromide were evaporated. The residue was taken into 150 ml of toluene, washed with a 5% aqueous solution of potassium hydroxide and water in this sequence, and dried over anhydrous sodium sulfate. Toluene was evaporated, and the residue was distilled under reduced pressure to give 7.2 g of 2-[2,6-dichloro-4-(2,2,2-trifluoroethylthio)-phenoxy]-ethyl bromide with the b.p.=124°–126° C./0.8 mmHg.

The following compounds of the formula (VIa) (this means compounds of the general formula (VI) wherein "Hal" is Br)

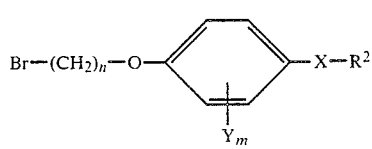

were obtained by the method described in Example VI-1:

| Compound | n | $Y_m$ | $X-R^2$ | b.p. °C./mmHg |
|---|---|---|---|---|
| VI-2 | 2 | — | —$SCH_2CF_3$ | 136–139/10 |
| VI-3 | 3 | — | —$SCH_2CF_3$ | 140–144/10 |
| VI-4 | 4 | — | —$SCH_2CF_3$ | 143–145/5 |
| VI-5 | 5 | — | —$SCH_2CF_3$ | 135–140/1.5 |
| VI-6 | 6 | — | —$SCH_2CF_3$ | 145–150/1.5 |
| VI-7 | 2 | 2-$CH_3$ | —$SCH_2CF_3$ | 114–116/0.8 |
| VI-8 | 4 | 2-$CH_3$ | —$SCH_2CF_3$ | 126–129/0.8 |
| VI-9 | 2 | 3,5-$(CH_3)_2$ | —$SCH_2CF_3$ | 123–125/2 |
| VI-10 | 4 | 3,5-$(CH_3)_2$ | —$SCH_2CF_3$ | 132–134/1 |
| VI-11 | 2 | 2-Cl | —$SCH_2CF_3$ | 118–120/0.8 |
| VI-12 | 4 | 2-Cl | —$SCH_2CF_3$ | 135–137/1 |
| VI-13 | 2 | 2,6-$Cl_2$ | —$SCH_2CF_3$ | 124–126/0.8 |
| VI-14 | 3 | 2,6-$Cl_2$ | —$SCH_2CF_3$ | 151–153/1.5 |
| VI-15 | 4 | 2,6-$Cl_2$ | —$SCH_2CF_3$ | 137–139/0.8 |
| VI-16 | 5 | 2,6-$Cl_2$ | —$SCH_2CF_3$ | 143–145/0.6 |
| VI-17 | 2 | — | —$OCF_3$ | 90–91/0.4 |
| VI-18 | 3 | — | —$OCF_3$ | 105–106/3.8 |
| VI-19 | 5 | — | —$OCF_3$ | 133–135/3.7 |
| VI-20 | 2 | 2-Cl | —$OCF_3$ | 105–107/3.7 |
| VI-21 | 3 | 2-Cl | —$OCF_3$ | 118–119/3.7 |
| VI-22 | 5 | 2-Cl | —$OCF_3$ | 144–146/3.7 |
| VI-23 | 2 | 2,6-$Cl_2$ | —$OCF_3$ | 111–113/3.7 |
| VI-24 | 3 | 2,6-$Cl_2$ | —$OCF_3$ | 125–127/3.7 |
| VI-25 | 4 | 2,6-$Cl_2$ | —$OCF_3$ | 136–138/3.7 |
| VI-26 | 5 | 2,6-$Cl_2$ | —$OCF_3$ | 145–148/3.7 |
| VI-27 | 2 | — | —$SCF_3$ | 85–90/0.75 |
| VI-28 | 3 | — | —$SCF_3$ | 105–108/0.82 |
| VI-29 | 4 | — | —$SCF_3$ | 105–108/0.75 |
| VI-30 | 5 | — | —$SCF_3$ | 115–120/0.75 |
| VI-31 | 2 | 2-Cl | —$SCF_3$ | 105–106/0.75 |
| VI-32 | 3 | 2-Cl | —$SCF_3$ | 116–117/0.68 |
| VI-33 | 4 | 2-Cl | —$SCF_3$ | 134–136/0.6 |
| VI-34 | 5 | 2-Cl | —$SCF_3$ | 140–142/0.75 |
| VI-35 | 2 | 2,6-$Cl_2$ | —$SCF_3$ | 114–116/0.75 |
| VI-36 | 3 | 2,6-$Cl_2$ | —$SCF_3$ | 113–120/0.6 |
| VI-37 | 4 | 2,6-$Cl_2$ | —$SCF_3$ | 130–132/0.75 |
| VI-38 | 5 | 2,6-$Cl_2$ | —$SCF_3$ | 142–145/0.64 |

Note: The symbol "—" in the column of $Y_m$ means there is no Y-substituent and the meaning of m is 0 (zero).

Example VIII-1

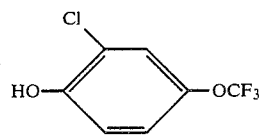

Gaseous chlorine was slowly introduced to a stirred solution of 35.6 g of 4-trifluoromethoxyphenol in 100 ml carbon tetrachloride. The reaction temperature was kept at 20° to 30° C. by outer cooling. After saturaring with chlorine, the reaction mixture was stirred at 20° to 30° C. for 1 hour, cooled, washed with water, dried over anhydrous sodium sulfate, and evaporated to give a pale yellow residue. The residue was distilled under reduced pressure to give 29.8 g of 2-chloro-4-trifluoromethoxyphenol which boiled at 67°–70° C./18 mmHg.

Example VIII-2

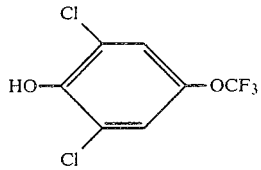

To a boiling solution of 21.3 g of 2-chloro-4-trifloromethoxyphenol, 2 g of anhydrous ferric chloride and 100 ml of carbon tetrachloride were introduced more than 8 g of gaseous chlorine over 1 hour. The reaction mixture was boiled another 1 hour, cooled, washed with water, dried over anhydrous sodium sulfate, and evaporated to give a pale yellow residue. The residue was distilled under reduced pressure (18 mmHg) and 9 g of a fraction which boiled at 96° to 99° C. was collected. When cooled, the fraction solidified. It melted at 42°–44° C.

Example VIII-3

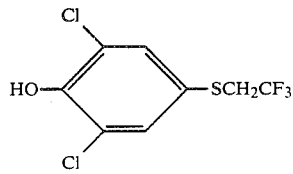

64 g of potassium carbonate were added to a solution of 41.9 g of 3,5-dichloro-4-hydroxy-benzenethiol in 200 ml of N,N-dimethylformamide under nitrogen atmosphere. To the stirred mixture were dropped at 30° to 40° C. 55 g of 2,2,2-trifluoroethyl-benzenesulfonate. The whole was stirred at 60° to 70° C. for 6 hours, cooled, mixed with 1.5 l of water, and acidified to pH 2 by dropwise addition of hydrochloric acid. A resulted oil was extracted with toluene and the toluene extract was washed with water. The washed toluene extracted was stirred with 160 ml of a 25% aqueous potassium hydroxide solution, and a water layer was separated. Then the separated water layer was acidified to pH 2 by adding hydrochloric acid. A resulted oil was extracted with toluene. The toluene extract was washed with water, dried over anhydrous sodium sulphate, and evaporated to give a residue. The residue was distilled under reduced pressure to give 42.3 g of 2,6-dichloro-4-(2,2,2-trifluoroethylthio)-phenol which boiled at 85° to 88° C./1 mmHg.

Example VIII-4

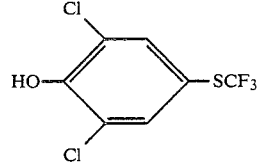

In the same way as shown in Example VIII-3, by using trifluoroiodomethane in place of 2,2,2-trifluoroethylbenzenesulfonate, 2,6-dichloro-4-trifluoromethylthio-phenol with the b.p. 110°–112° C./18 mmHg and the m.p. 38°–40° C. was prepared.

USE EXAMPLES

The known comparison compounds are identified as follows:

Comparison Compound A-1:

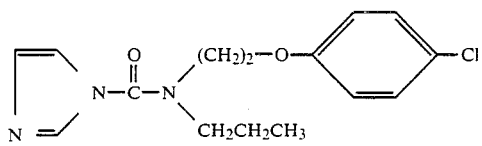

Comparison Compound A-2:

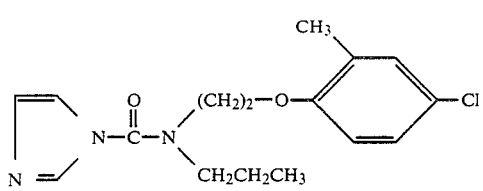

Both compounds shown above are described in the Japanese Laid Open Application No. 31047/1975 resp. the GB-PS No. 1 469 779.

EXAMPLE A

Rice blast (*Pyricularia oryzae*) test (testing by spraying on stalks and leaves)

Active compound: 50 parts by weight
Carrier: 45 parts by weight of a 1:5 mixture of of diatomaceous earth and kaolin
Emulsifier: 5 parts by weight of polyoxyethylene alkyl phenyl ether The active compound, carrier and emulsifier in the the amounts indicated above were pulverized and mixed to form a wettable powder. The test chemical was prepared by diluting a predetermined amount of the wettable powder with water.

Testing method

Aquatic rice plants (variety: Asahi) were cultivated in unglazed pots having a diameter of 12 cm, and in 3- to 4-leaf stage, a dilution to a predetermined concentration of the test chemical prepared as above was sprayed at a rate of 50 ml per three pots. On the next day, a suspension of artificially cultivated spores of *Pyricularia oryzae* was inoculated (twice) by spraying. The pots were maintained in a humid chamber kept at a relatively humidity of 100% and a temperature of 25° C. to infect the plants with the fungus. Seven days after the inoculation, the degree of the disease per pot was evaluated and rated on the following standard, and the control index (%) was calculated. The phytotoxicity was also examined.

| Degree of disease | Percentage of the area of lesions (%) |
|---|---|
| 0 | 0 |
| 0.5 | 2 or less |
| 1 | 3–5 |
| 2 | 6–10 |
| 3 | 11–20 |
| 4 | 21–40 |
| 5 | 41 or more |

$$\text{Control index (\%)} = \frac{\text{Degree of disease in the non-treated plots} - \text{Degree of disease in the treated plots}}{\text{Degree of disease in the non-treated plots}} \times 100$$

In the present test, three pots constituted one treatment The results are shown in the following Table:

TABLE A

Rice blast (*Pyricularia oryzae*) test

| Compound No. | Concentration of the active ingredient ppm | Control index (%) |
|---|---|---|
| A-1 (Comparison compound) | 250 | 40 |
| 1 | 250 | 100 |
| 16 | 250 | 100 |
| 18 | 250 | 100 |
| 21 | 250 | 100 |
| 23 | 250 | 100 |
| 31 | 250 | 100 |
| 40 | 250 | 100 |
| 42 | 250 | 100 |
| 46 | 250 | 100 |
| 65 | 250 | 100 |
| 68 | 250 | 100 |

EXAMPLE B

Late blight of tomato (*Phytophtora infestans*) test

Each of the test compounds in the form of an emulsion prepared in accordance with Example (b) (see hereinafter) was sprayed by a spray gun on tomato (variety: Kurihara) grown in 9 cm unglazed pots. One day after the spraying, a suspension of spores of the present pathogen was inoculated and the pots were left to stand overnight in a constant temperature chamber kept at a temperature of 22° C. and a humidity of at least 90%. Five days later, the degree of disease was rated on the following standards by the percentage of the area of lesions, and the control index was calculated.

| Degree of disease | Percentage of the area of lesions (%) |
|---|---|
| 0 | 0 |
| 0.5 | 2 or less |
| 1 | 3–5 |
| 2 | 6–15 |
| 3 | 16–30 |
| 4 | 31–50 |
| 5 | 51 or more |

$$\text{Control index (\%)} = \frac{\text{Degree of disease in the non-treated plots} - \text{Degree of disease in the treated plots}}{\text{Degree of disease in the non-treated plots}} \times 100$$

The results are shown in the following Table:

TABLE B

Late blight of tomato (*Phytophtora infestans*) test

| Compound No. | Concentration of the active ingredient ppm | Control index (%) |
|---|---|---|
| A-1 (Comparison compound) | 1000 | 35 |
|  | 500 | 0 |
| A-2 (Comparison compound) | 1000 | 40 |
|  | 500 | 0 |
| 6 | 500 | 100 |
| 23 | 500 | 100 |
| 25 | 500 | 100 |
| 32 | 500 | 100 |
| 36 | 500 | 100 |
| 45 | 500 | 100 |
| 66 | 500 | 100 |

EXAMPLE C

Anthracnose of cucumber (*Colletotrichum lagenarium*) test

Each of the test compounds in the form of an emulsifiable concentrate prepared as in Example (b) (see hereinafter) was sprayed by means of a spray gun on two-leaf stage cucumber (variety: Yotsuba) cultivated in 9 cm unglazed pots. One day after the spraying, a spore suspension of the present pathogen (*Colletotrichum lagenarium*) was inoculated by spraying, and the pots were left to stand overnight in a constant temperature chamber kept at 23° C. and a humidity of more than 90%. Six days later, the degree of disease was determined by the percentage of the area of lesions as in Example B, and the control index was also calculated.

The results are shown in the following Table:

TABLE C

Anthracnose of cucumber (*Collerotrichum lagenarium*) test

| Compound No. | Concentration of the active ingredient ppm | Control index (%) |
|---|---|---|
| A-2 (comparison compound) | 250 | 35 |
| 1 | 250 | 100 |
| 23 | 250 | 100 |
| 31 | 250 | 100 |
| 32 | 250 | 100 |
| 36 | 250 | 100 |
| 40 | 250 | 100 |
| 65 | 250 | 100 |
| 68 | 250 | 100 |
| 69 | 250 | 100 |
| 73 | 250 | 100 |
| 75 | 250 | 100 |
| 78 | 250 | 100 |
| 79 | 250 | 100 |
| 81 | 250 | 100 |

EXAMPLE D

Powdery mildew of cucumber (*Sphaerotheca fuliginea*) test

Each of the test compounds in the form of an emulsifiable concentrate prepared as in Example (b) (see hereinafter) was sprayed by means of a spray gun on cucumber in the two-leaf stage (variety: Tokiwa, crawling type) cultivated in 9 cm unglazed pots. One day after the spraying, a spore suspension of the present pathogen (*Sphaerotheca fuliginea*) was inoculated by spraying, and the pots were left to stand in a constant temperature chamber kept at 23° C. Ten days later, the degree of disease was determined by the percentage of the area of lesions as in Example B, and the control index was also calculated.

The results are shown in the following Table:

TABLE D

Powdery mildew of cucumber (*Sphaerotheca fuliginea*) test

| Compound No. | Concentration of the active ingredient ppm | Control index (%) |
|---|---|---|
| A-1 (comparison compound) | 100 | 40 |
|  | 50 | 0 |
| A-2 (comparison compound) | 100 | 0 |
|  | 50 | 100 |
| 6 | 50 | 100 |
| 7 | 50 | 100 |
| 37 | 50 | 100 |
| 41 | 50 | 100 |
| 42 | 50 | 100 |
| 43 | 50 | 100 |
| 44 | 50 | 100 |
| 46 | 50 | 100 |
| 50 | 50 | 100 |
| 51 | 50 | 100 |
| 52 | 50 | 100 |
| 53 | 50 | 100 |
| 54 | 50 | 100 |
| 58 | 50 | 100 |
| 59 | 50 | 100 |
| 62 | 50 | 100 |
| 63 | 50 | 100 |
| 68 | 50 | 100 |

EXAMPLE E

*Helminthosporium oryzae* test (efficacy by stalk/leave spraying)

Rice plants (variety: kusabue) were cultivated in unglazed pots having a diameter of 12 cm, and in the 3- to 4-leaf stages, a dilution of each of the test compounds prepared in accordance with Example 14 hereinafter was sprayed at a rate of 50 ml per three pots. On the next day, a suspension of artificially cultivated spores of *Helminthosporium oryzae* was sprayed twice onto the pots. The pots were maintained in a humid chamber having a relative humidity of 10% and a temperature of 25° C. to induce infection. Seven days after the inoculation, the degree of disease per pot was rated on a scale of 0 to 5 as follows, and the control index (%) was calculated.

| Degree of disease | Extent of disease |
|---|---|
| 0 | No disease |
| 1 | Slight |
| 2 | Small |
| 3 | Medium |
| 4 | Great |
| 5 | Very great |

$$\text{Control index (\%)} = \frac{\text{Degree of disease in the non-treated plots} - \text{Degree of disease in the treated plots}}{\text{Degree of disease in the non-treated plots}} \times 100$$

In this test, three pots constituted one treatment. The results are shown in the following Table:

TABLE E

| | Helminthosporium oryzae (test (efficacy by stalk/leave spraying)) | |
|---|---|---|
| Compound No. | Concentration of the active ingredient ppm | Control index (%) |
| A-1 (comparison compound) | 250<br>100 | 50<br>10 |
| A-2 comparison compound) | 250<br>100 | 40<br>10 |
| 1 | 100 | 100 |
| 6 | 100 | 100 |
| 36 | 100 | 100 |
| 42 | 100 | 100 |
| 48 | 100 | 100 |
| 64 | 100 | 100 |
| 68 | 100 | 100 |

EXAMPLE F

Brown spot of rice (*Helminthosporium oryzae*) test/seed treatment

Seeds (variety: Koshihikari) spontaneously infected at a high rate with rice brown spot (*Helminthosporium oryzae*) were treated with a dilution in a predetermined concentration shown in the following table of each of the test compounds, prepared as in the method of Example (a) (see hereinafter) by each of the methods shown in the following table. On the next day, the treated seeds were sown in a seedling growing box and grown by an ordinary method. Fifteen days after the sowing, all of the seedlings were pulled out, and divided into diseased seedlings and sound seedlings. The control index was calculated in accordance with the following equation from the percentage of the sound seedlings based on the total number of seedlings based on the total number of seeds sown. The results are shown in Table F.

$$\text{Control index (\%)} = 100 - \left[ \frac{100 - \text{percentage of sound seedlings in the treated plots}}{100 - \text{percentage of sound seedlings in the non-treated plots}} \times 100 \right]$$

In the table, the methods of treatment were as follows:
M-1: the seeds were immersed for 1/6 hour
M-2: the seeds were immersed for 20 hours
M-3: the seeds were covered with the powder of the compound

TABLE F

Brown spot of rice (*Helminthosporium oryzae*) test/seed treatment

| Compound No. | Concentration of the active ingredient | Testing method | Percentage germination (%) | Percentage of diseased seedlings based on the seeds that germinated (%) | Percentage of sound seedlings based on the sown seeds (%) | Control index (%) |
|---|---|---|---|---|---|---|
| Non-treated | — | — | 44.3 | 57.5 | 18.8 | 0 |
| A-1 (Comparison compound) | 0.25% | M-1 | 62.3 | 38.7 | 38.4 | 24 |
| | 0.025% | M-2 | 48.7 | 41.7 | 28.4 | 12 |
| | 0.25 g/kg seeds | M-3 | 56.0 | 39.7 | 33.8 | 18 |
| 1 | 0.25% | M-1 | 91 | 0 | 91 | 89 |
| | 0.025% | M-2 | 89 | 1.5 | 87.7 | 85 |
| | 0.25 g/kg seeds | M-3 | 90 | 0 | 90 | 88 |
| 42 | 0.25% | M-1 | 92 | 0 | 92 | 90 |
| | 0.025% | M-2 | 90 | 0.5 | 89.6 | 87 |
| | 0.25 g/kg seeds | M-3 | 90 | 0 | 90 | 88 |
| 68 | 0.25% | M-1 | 90 | 0 | 90 | 88 |
| | 0.025% | M-2 | 90 | 0 | 90 | 88 |
| | 0.25 g/kg seeds | M-3 | 90 | 0 | 90 | 88 |

Note:
The control index is the average value of three test areas each consisting of 300 seeds.

EXAMPLE G

"Bakanae disease" of rice (*Gibberella fujikuroi*) test/seed treatment

Seeds (variety: Koshihikari) spontaneously infected with "bakanae" disease of rice (*Gibberella fujikuroi*) were immersed for the period of time shown in the following table in a dilution in a predetermined concentration shown in the following table prepared in accordance with Example (a) (see hereinafter). The treated seeds were air-dried, and sown in a rice seedling growing box, and grown by an ordinary method. Up to 20 days after the sowing, the diseased seedlings were periodically pulled out and examined, and the control index (%) was calculated in accordance with the following equation. The results are shown in Table G.

$$\text{Control index (\%)} = \frac{\text{percentage of diseased seedlings in the treated plots}}{\text{Percentage of diseased seedlings in the non-treated plots}} \times 100$$

The control index shows an average value of three testing areas with one area consisting of 300 seeds.

TABLE G

"Bakanae disease" of rice (*Gibberella fujikuroi*) test/seed treatment

| Compound No. | Concentration of the active ingredient (%) | Immersing time (hrs) | Control index (%) |
|---|---|---|---|
| A-1 (comparison compound) | 0.5 | 1/6 | 75 |
|  | 0.25 | 1/6 | 30 |
|  | 0.05 | 20 | 75 |
|  | 0.025 | 20 | 28 |
| 1 | 0.5 | 1/6 | 100 |
|  | 0.25 | 1/6 | 100 |
|  | 0.125 | 1/6 | 100 |
|  | 0.05 | 20 | 100 |
|  | 0.025 | 20 | 100 |
|  | 0.0125 | 20 | 100 |
| 42 | 0.5 | 1/6 | 100 |
|  | 0.25 | 1/6 | 100 |
|  | 0.125 | 1/6 | 100 |
|  | 0.05 | 20 | 100 |
|  | 0.025 | 20 | 100 |
|  | 0.0125 | 20 | 100 |
| 68 | 0.5 | 1/6 | 100 |
|  | 0.25 | 1/6 | 100 |
|  | 0.125 | 1/6 | 100 |
|  | 0.05 | 20 | 100 |
|  | 0.025 | 20 | 100 |
|  | 0.0125 | 20 | 100 |

EXAMPLE H

MBC-resistant "bakanae disease" of rice fungus (*Gibberella fujikuroi*) test/seed treatment The "MBC-resistant bakanae disease of rice fungus" means a fungus which shows resistance to Benomyl (1-(N-n-butylcarbamoyl)-2-(methoxycarboxamido)-benzimidazole), Thiophannate-methyl (1,1'-o-phenylene-bis(3,3'-methoxycarbonyl-thiourea)) and HBC (or Carbendazim, which is benzimidazole-2-carbamide-acid-methyl-ester).

MBC-resistant "bakanae" disease fungus (the minimum growth inhibition concentration in vitro with respect to benomyl was 800 ppm) was sprayed onto rice (variety: Koshihikari) in the flowering stage. The resulting infected seeds were treated by immersion in the same way as in Example G. The results are shown in Table G. The control index was an average of three testing areas with one area consisting of 300 seeds.

TABLE H

MBC-resistant "bakanae disease" of rice fungus (*Gibberella fujikuroi*) test/seed treatment

| Compound No. | Concentration of the active ingredient (%) | Immersing time (hrs) | Control index (%) |
|---|---|---|---|
| A-1 (Comparison compound) | 0.05 | 20 | 45 |
| 68 | 0.025 | 20 | 100 |

FORMULATION EXAMPLES

Example (a) (wettable powder)

Fifteen parts of compound No. 1 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and sprayed onto pathogens and/or the locus of their occurrence and the locus of occurrence of crop diseases.

Example (b) (emulsifiable concentrate)

Thirty parts of compound No. 2 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto pathogens and/or the locus of their occurrence and the locus of occurrence of crop diseases.

Example (c) (dust)

Two parts of compound No. 3 of the invention and 98 parts of powdery clay are pulverized and mixed to form a dust. It is scattered over pathogens and/or the locus of their occurrence and the locus of occurrence of crop diseases.

Example (d) (dust)

Compound No. 4 of the invention (1.5 parts), 0.5 part of isopropyl hydrogen phosphate and 98 parts of powdery clay are pulverized and mixed to form a dust. It is scattered over pathogens and/or the locus of their occurrence and the locus of occurrence of crop diseases.

Example (e) (granules)

Water (25 parts) is added to a mixture consisting of 10 parts of compound No. 3 of the invention, 30 parts of bentonite (montmorrillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over pathogens and/or the locus of occurrence of crop diseases.

We claim:

1. Carbamoylimidazole derivatives represented by the general formula (I)

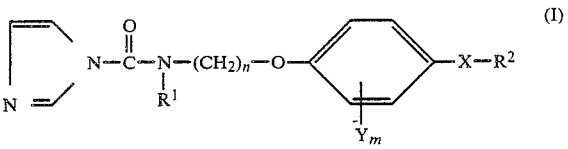

in which
R¹ represents lower alkyl, lower alkoxy—lower alkyl or cycloalkyl having 3 to 8 carbon atoms,
R² represents fluoro-substituted lower alkyl,
X represents oxygen or sulfur,
Y represents halogen or lower alkyl,
m represents the numbers 0, 1 or 2, and
n represents the numbers 2, 3, 4, 5 or 6.

2. Compounds of the general formula (I) claimed in claim 1, wherein
R¹ represents alkyl with 1 to 4 carbon atoms, alkoxyalkyl with altogether 2 to 4 carbon atoms or cycloalkyl with 5 to 6 carbon atoms,
R² represents fluoroalkyl with 1 to 4 carbon atoms and 1 to 3 fluorine atoms,
Y represents chlorine or methyl, and
X, m and n have the meanings given above.

3. 1-(N-2-[2,6-dichloro-4-(2,2,2-trifluoroethylthio)-phenoxy]-ethyl-N-propylcarbamoyl)-imidazole according to claim 1 which is represented by the formula:

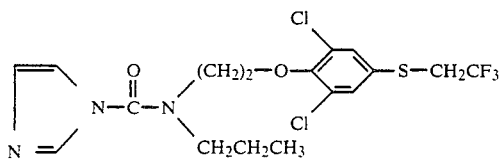

4. 1-(N-2-(2,6-dichloro-4-trifluoromethylthiophenyl)ethyl-N-propylcarbamoyl]-imidazole according to claim 1 which is represented by the formula:

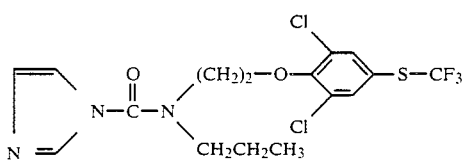

5. 1-[v-2-(2,6-dichloro-4-trifluoromethoxyphenoxy)ethyl-N-propylcarbamoyl]-imidazole according to claim 1 which is represented by the formula:

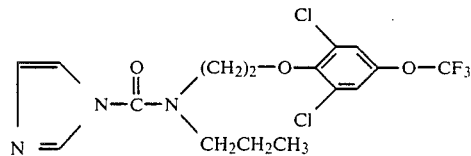

6. A fungicidal composition comprising a fungicidally effective amount of a compound according to claim 1 in admixture with a diluent.

7. A method of combating fungi which comprises applying to such fungi or to a fungus habitat a fungicidally effective amount of a compound according to claim 1.

8. The method according to claim 7 whereas such compound is 1-(N-2[2,6-dichloro-4-(2,2,2-trifluoroethylthio)-phenoxy]ethyl-N-propylcarbamoyl)-imidazole, 1-[N-2-(2,6-dichloro-4-trifluoromethylthiophenyl)-ethyl-N-propylcarbamoyl]-imidazole or 1-[-2-(2,6-dichloro-4-trifluoromethoxyphenoxy)-ethyl-N-propylcarbamoyl]-imidazole.

* * * * *